US012680996B2

(12) United States Patent (10) Patent No.: US 12,680,996 B2
Godbole et al. (45) Date of Patent: Jul. 14, 2026

(54) CROP MONITORING SYSTEM AND METHOD

(71) Applicant: AGCO Corporation, Duluth, GA (US)

(72) Inventors: Ravindra Godbole, Duluth, GA (US); Darren Goebel, Duluth, GA (US)

(73) Assignee: AGCO Corporation, Duluth, GA (US)

( * ) Notice: Subject to any disclaimer, the term of this patent is extended or adjusted under 35 U.S.C. 154(b) by 245 days.

(21) Appl. No.: 18/552,721

(22) PCT Filed: Apr. 13, 2022

(86) PCT No.: PCT/IB2022/053484
§ 371 (c)(1),
(2) Date: Sep. 27, 2023

(87) PCT Pub. No.: WO2022/234370
PCT Pub. Date: Nov. 10, 2022

(65) Prior Publication Data
US 2024/0167994 A1 May 23, 2024

Related U.S. Application Data

(60) Provisional application No. 63/184,414, filed on May 5, 2021.

(51) Int. Cl.
*G01N 33/00* (2006.01)
(52) U.S. Cl.
CPC ................................ *G01N 33/0098* (2013.01)
(58) Field of Classification Search
None
See application file for complete search history.

(56) References Cited

U.S. PATENT DOCUMENTS 6,073,427 A * 6/2000 Nichols .............. A01D 41/1271
460/7
6,178,253 B1 1/2001 Hendrickson et al.
(Continued)

FOREIGN PATENT DOCUMENTS

CN 107741444 A 2/2018
CN 109769533 * 5/2019 ............. A01C 23/04
(Continued)

OTHER PUBLICATIONS

Wilson AD. Diverse applications of electronic-nose technologies in agriculture and forestry. Sensors (Basel). Feb. 8, 2013;13(2):2295-348. doi: 10.3390/s130202295. PMID: 23396191; PMCID: PMC3649433. (Year: 2013).*

(Continued)

*Primary Examiner* — Beniyam Menberu

(57) ABSTRACT

A crop monitoring system includes one or more sensors adapted to sense a stalk of a growing crop and generate a detection signal that is representative of the diameter of the stalk. A processor is configured to generate a nutrient status indicator from the detection signal. The nutrient status indicator may also depend partially on VOCs (volatile organic carbon compounds) released by the growing crop. A user interface device is configured to display the nutrient status indicator for use in a crop management system. Related methods are also disclosed, and may be used earlier than conventional nutrient inspection methods, for example, after maize plants have at least six leaves.

18 Claims, 3 Drawing Sheets

(56)          References Cited

U.S. PATENT DOCUMENTS

| | | | |
|---|---|---|---|
| 7,837,844 B2 | 11/2010 | Patel et al. | |
| 9,581,433 B2 | 2/2017 | Tixier et al. | |
| 9,652,840 B1 * | 5/2017 | Shriver | G01N 33/24 |
| 2014/0127672 A1 | 5/2014 | Davis et al. | |
| 2014/0230391 A1 | 8/2014 | Hendrickson et al. | |
| 2015/0015697 A1 | 1/2015 | Redden et al. | |
| 2018/0143172 A1 | 5/2018 | McPeek | |
| 2019/0137476 A1 | 5/2019 | Davis et al. | |
| 2020/0116694 A1 * | 4/2020 | Rinaldi | G01N 27/125 |
| 2021/0149406 A1 * | 5/2021 | Javault | A01C 21/005 |
| 2021/0316857 A1 * | 10/2021 | Yanagishita | A01G 7/00 |
| 2021/0321602 A1 | 10/2021 | McMenamy | |
| 2022/0064076 A1 * | 3/2022 | Slezack-Deschaumes | C12N 1/20 |
| 2022/0104441 A1 * | 4/2022 | Charling | A01G 25/16 |
| 2022/0221348 A1 * | 7/2022 | John | G01K 7/02 |
| 2022/0365054 A1 | 11/2022 | Godbole et al. | |

FOREIGN PATENT DOCUMENTS

| | | | | |
|---|---|---|---|---|
| GB | 2562275 A | | 11/2018 | |
| JP | H08172912 | * | 7/1996 | A01G 7/00 |
| JP | 2004008186 | * | 1/2004 | G05D 1/0219 |
| JP | 2016065868 | * | 4/2016 | A01G 7/00 |
| JP | 2018082648 | * | 5/2018 | A01C 21/00 |
| JP | 2020137415 | * | 9/2020 | A01G 27/00 |

OTHER PUBLICATIONS

Kigathi RN, Weisser WW, Reichelt M, Gershenzon J, Unsicker SB. Plant volatile emission depends on the species composition of the neighboring plant community. BMC Plant Biol. Feb. 6, 2019;19(1):58 (Year: 2019).*

European Patent Office, Search Report for related PCT Application No. PCT/IB2022/053484, dated Jul. 26, 2022, 12 pages.

Checco Alessandro et al: "Internet of Trees: A vision for advanced monitoring of crops", Conference on Sensor Networks, 2020, pp. 182-186, DOI: 10.5220/0009368801820186.

Aksenov Alexander A. et al: "Volatile Organic Compounds (VOCs) for Noninvasive Plant Diagnostics", American Chemical Society/ Oxford University Press, US, ISSN: 0097-6156, vol. 1141, pp. 73-95, DOI: 10.1021/pk-2013-1141.

Fernandez J. et al: "Irrigation scheduling from stem diameter variations: a review", Agricultural and Forest Meteorology, Elsevier, Amsterdam, vol. 150, 2010, pp. 135-151, ISSN: 0168-1923.

* cited by examiner

110

500

CROP MONITORING SYSTEM AND METHOD

CROSS-REFERENCE TO RELATED APPLICATION

This application is a national phase entry under 35 U.S.C. § 371 of International Patent Application PCT/IB2022/053484, filed Apr. 13, 2022, designating the United States of America and published in English as International Patent Publication WO 2022/234370 A1 on Nov. 10, 2022, which claims the benefit of the filing date of U.S. Provisional Patent Application 63/184,414, "Crop Monitoring System and Method," filed May 5, 2021, the entire disclosure of which is incorporated herein by reference.

FIELD

The disclosure relates to the monitoring of crops and particularly, but not exclusively so, to the monitoring of a nutrient status of agricultural crops.

BACKGROUND

Traditionally, crops are monitored visually by growers who regularly walk crop fields throughout the growing season. Crops are monitored for problematic weeds, pests, and diseases. Crops may show visual symptoms of stress caused by nutrient deficiency, which may be discovered by walking the crop. In more recent times, technology has been used to monitor crops remotely from satellites or drones. Furthermore, agronomic challenges may be predicted through modelling using past cropping records, weather records, specific crop demands, and varietal resistance by way of example. Soil and tissue testing are also commonly undertaken to obtain a more precise assessment of disease or nutrient levels.

The soil alone usually cannot supply the nutrients required to grow a crop with optimized profit. As such, one or more applications of fertilizer are made, these often being in significant quantities for macronutrients such as nitrogen, phosphorus, and potassium. It is understood that the quantity and timing of fertilizer applications should be selected to minimize pollution and waste and operating costs while meeting the requirements of the growing crop to optimize yield and thus profit. This is especially true of nitrogen, which is critical for protein building and is prone to leaching through the soil profile.

Maximum yields are achieved with plants that never experience deficiency or stress. However, a deficiency can be identified and "corrected" with fertilization to improve yield potential. The earlier a deficiency is detected, the greater the benefit will be to fertilize.

BRIEF SUMMARY

In some embodiments, a crop monitoring system includes at least one sensor configured to sense a stalk of a growing crop and generate a detection signal that is representative of the diameter of the stalk, a processor in communication with the at least one sensor and configured to generate a nutrient status indicator from the detection signal, and a user interface device in communication with the processor and configured to display the nutrient status indicator.

Stalk diameter is a reliable indicator of plant stress at certain periods of growth. In maize, stalk diameter can typically be used to detect nutrient deficiency when the plants have at least six (6) leaves. Plants also release volatile and non-volatile chemicals at various stages throughout the growing season, both under and above the soil. Stresses caused by nutrient deficiency or disease have been found to affect the VOCs released. The relationship between plant stress, stalk diameter, and/or VOCs may be used to provide an early warning of crop stress to a grower. Advantageously, this enables a grower to take corrective action earlier than with known monitoring systems.

In one embodiment, the sensor(s) may include a soil sensor adapted to detect VOCs under the soil surface. The soil sensor may, for example, include a ground probe having a sensor attached thereto.

In another embodiment, the sensor(s) include a non-contact sensor adapted for placement under a crop canopy to detect VOCs emitted by the growing crop above a soil surface.

In yet another embodiment, the sensor(s) include a contact sensor adapted for placement on plant tissue of the growing crop to detect VOCs emitted by the growing crop.

In one embodiment, the sensor(s) may include a camera or other optical device fixed in the field to detect stalk diameter.

In another embodiment, the sensor(s) include a vehicle-mounted sensor adapted to detect stalk diameter and/or VOCs emitted by the growing crop as the vehicle is driven over or around growing crop.

The sensor(s) may include one or more autonomous crop-scouting machines, each having a sensing device in wireless communication with the processor and adapted to detect stalk diameter and/or VOCs emitted by the growing crop.

Stressed crops release a VOC signature that is different to that released by healthy crops. By detecting and/or isolating certain VOC compounds released from a growing crop, an early indication of crop stress can be obtained and acted upon.

In one embodiment, the sensor(s) include a communicatively connected mesh or array of sensing devices for distribution across a crop field to provide a higher resolution monitoring system. The processor may be configured to receive a geolocation of each sensing device and generate a map representative of the crop field. The map may include a nutrient status indicator corresponding to each sensing device. The user interface device may display the map to a user.

In another embodiment, electronic storage is in communication with the processor. The storage is configured to store stalk diameter data and/or VOC signatures, and the processor is configured to compare the detection signal with the stored diameter data and/or VOC signatures to generate the nutrient status indicator.

In one embodiment, the processor is configured to generate a crop application recommendation that is dependent upon the nutrient status indicator, and the crop application recommendation is displayed by the user interface device. The crop application recommendation may be generated based upon a crop growth stage indicator.

The crop application recommendation may include a nitrogen application recommendation. Alternatively, the crop application recommendation may relate to a different macronutrient, a micronutrient, a pesticide, a growth regulator, etc.

In some embodiments, a method of monitoring a growing crop includes detecting stalk diameters and/or VOCs emitted by a growing crop and generating a plurality of signals, and processing the signals to generate nutrient status indicators for use in a crop management system.

BRIEF DESCRIPTION OF THE DRAWINGS

Further advantages will become apparent from the following description of specific embodiments with reference to the appended drawings in which.

DETAILED DESCRIPTION

While the disclosure will be described in connection with these drawings, there is no intent to limit to the embodiment or embodiments disclosed herein. Although the description identifies or describes specifics of one or more embodiments, such specifics are not necessarily part of every embodiment, nor are all various stated advantages necessarily associated with a single embodiment or all embodiments. On the contrary, the intent is to cover all alternatives, modifications, and equivalents included within the scope of the disclosure as defined by the appended claims. Further, it should be appreciated in the context of the present disclosure that the claims are not necessarily limited to the particular embodiments set out in the description.

Figure 1:
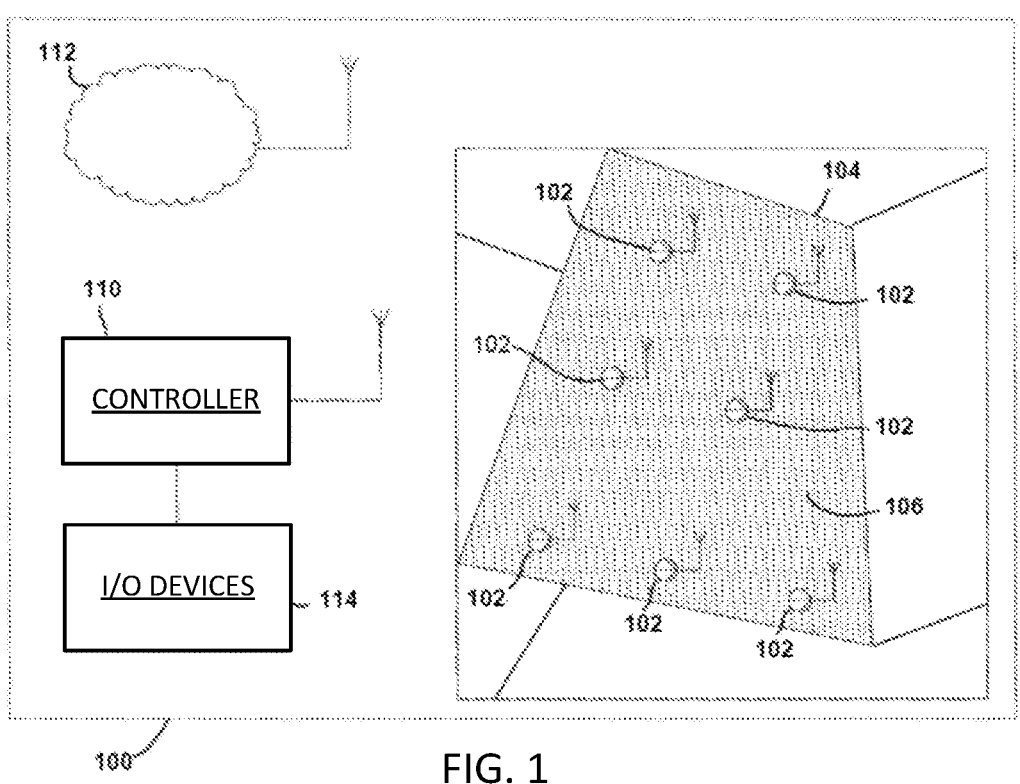
FIG. 1 is a schematic view of a crop monitoring system in accordance with one embodiment.

With reference to FIG. 1, a crop monitoring system 100 comprises a set of sensing devices 102 distributed across an agricultural field 104 containing a growing crop 106. The crop monitoring system 100 is not to be limited by the crop in which the system 100 is implemented but, for completeness and by way of example only, the crop may be maize, a cereal, canola, sorghum, milo, sugar cane, or other high-nitrogen-demand crops. It should also be understood that the system 100 may have application in non-agricultural crops such as horticultural crops including fruit and vegetable crops.

Each sensing device 102 serves to detect a property related to plant health or nutrient deficiency, such as stalk diameter or volatile organic chemicals released by the growing crop 106. Each sensing device 102 is in wireless communication with a controller 110 which may be located remote from the field 104, for example in a farm office. Although the illustrated embodiment shows a wireless interface between the sensing devices 102 and the controller 110, a wired, or partially wired, interface may be used instead. Moreover, the sensing devices 102 may communicate with the controller 110 via a cloud network represented schematically at 112.

Input/output devices represented generally at 114 are communicatively connected to the controller 110. The input/output devices may include a user interface device in the form of a touch-sensitive display that allows users to receive messages from the system 100 and enter commands.

Figure 2:
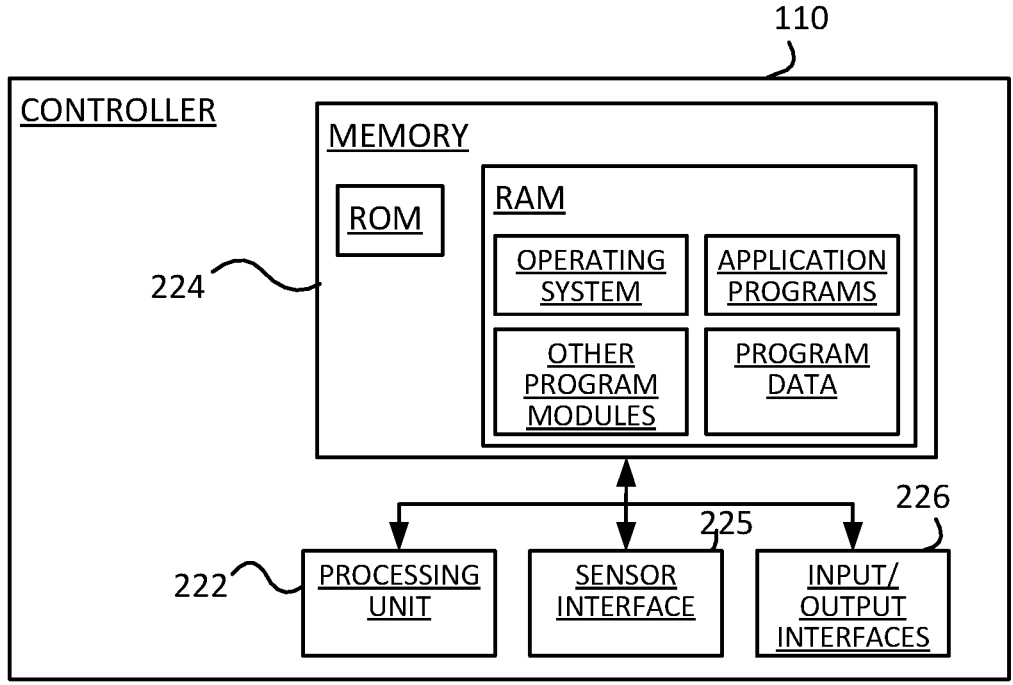
FIG. 2 is a block diagram of the controller of the system of FIG. 1.

FIG. 2 illustrates one embodiment of controller 110. Controller 110 can include a processing unit 222 and memory 224 coupled to the processing unit 222. In the illustrated example, the processing unit 222 is a computer processor with associated memory and timing circuitry (not separately shown) that is a functional part of the system and is activated by, and facilitates functionality of other parts or components of the system 100. Memory 224 can include computer storage media such as read only memory and random access memory. A number of program modules may be stored, such as application programs that can include instructions for the controller 110.

A sensor interface 225 can be configured to receive feedback from the sensors 102. I/O interfaces 226 can be configured to receive signals from input devices that are operated by the user and provide signals to output devices, such as the example display device mentioned above.

Figures 3, 4:
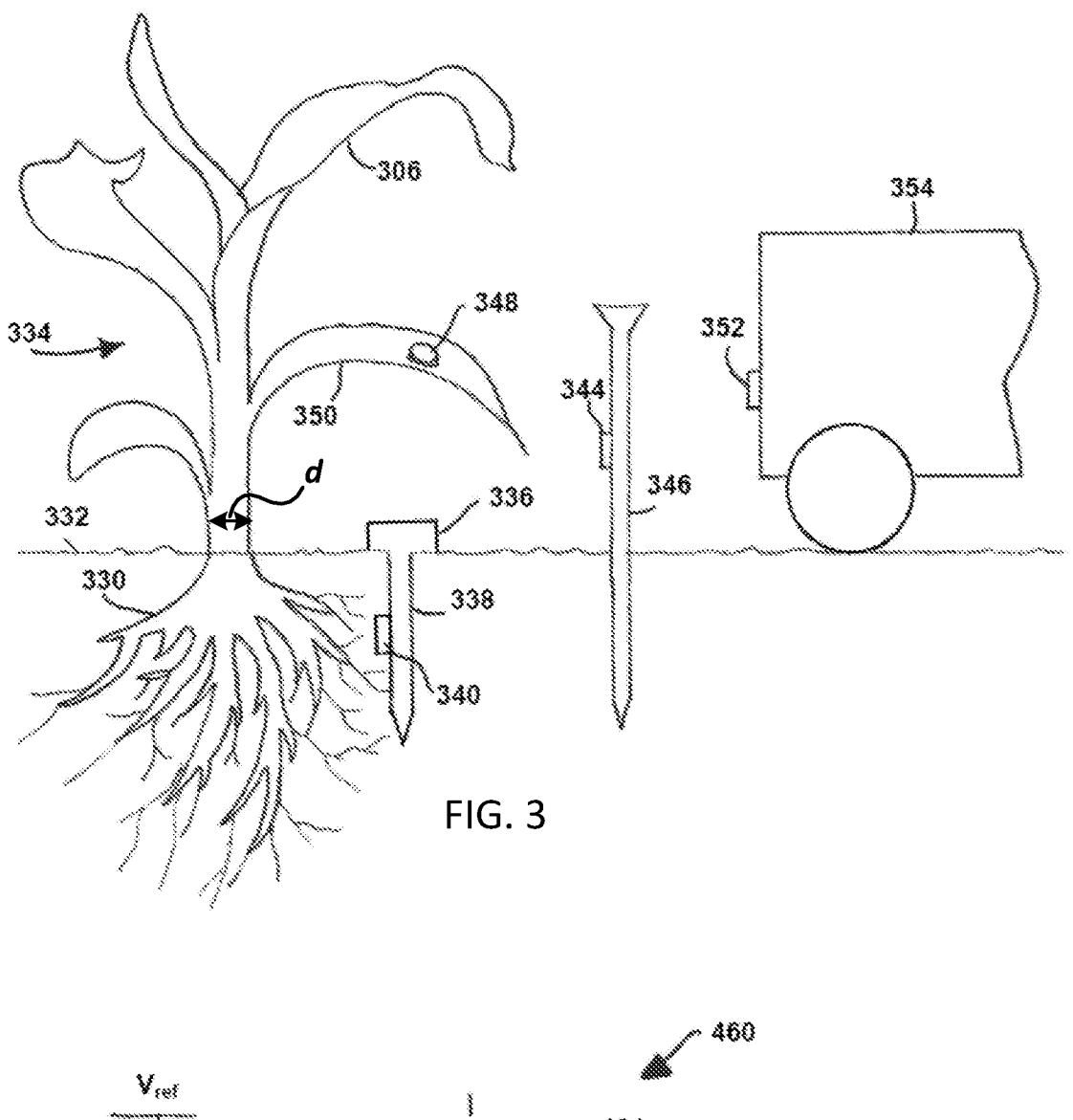
FIG. 3 is a schematic elevation of part of a crop monitoring system located in a field of a growing crop in accordance with an embodiment.
FIG. 4 is a schematic view of components of a sensing device for use in an embodiment.

Turning to FIG. 3, one maize plant 306 is illustrative of the plurality of plants in crop field 106. The plant 306 has a root network 330 extending below the ground surface 332 and an above-surface portion 334. FIG. 3 shows four different examples of sensor devices, which may correspond to sensor devices 102 shown in FIG. 1. It should be understood that various different sensing devices 102 can be employed to sense stalk diameter or capture and/or detect VOCs released by the growing crop. By way of example only, the sensor device 102 may be an interdigitated chemical sensor such as that disclosed in U.S. Pat. No. 7,837,844, "Interdigiated Chemical Sensors, and Methods of Making and Using the Same," granted Nov. 23, 2010, the entire disclosure of which is incorporated herein by reference. Alternatively, the sensor devices 102 may employ photoionization detection technology as used in commercially available handheld VOC detectors. The example types of sensor devices 102 described hereinafter may be used alone or in combination.

A soil sensor 336 is adapted for placement under the soil surface 332 to detect VOCs emitted by the root network 330 of the growing crop under the soil surface 332. The soil sensor 336 may include a ground stake 338 having a sensor 340 attached thereto (e.g., a thin-film sensor), and an above-surface portion 342 which houses a battery and a transmitter for communication with other sensing devices 102 and/or the controller 110.

A stationary non-contact sensor 344 is adapted for placement under the canopy of plant 306 to stalk diameter and/or detect VOCs emitted by the growing crop above a soil surface 332. The stationary non-contact sensor 344 may be anchored to the ground by attachment to a spike 346 inserted into the ground as illustrated.

A stationary contact sensor 348 is adapted for placement on plant tissue of the growing crop to detect VOCs emitted by the growing crop. For illustrative purposes, the sensor 348 is shown as being fixed to a lower leaf 350 of plant 306.

In an alternative embodiment, stalk diameter and/or plant-released VOCs may be captured and/or detected by a mobile, vehicle-mounted, sensor 352 adapted to detect VOCs emitted by the growing crop as a vehicle 354 is driven over the growing crop. The vehicle 354 is illustrated generally in FIG. 3 but may be, for example, an autonomous vehicle such as a scouting robot, an agricultural tractor, or a spraying machine by way of example. Such autonomous vehicles may be self-navigated or remotely controlled through the field. In other embodiments, the sensor 352 may be carried by an unmanned aerial vehicle (UAV, i.e., a drone) or even by a person walking the field.

The described sensing devices 340, 344, 348, 352 capture and/or detect VOCs released by the plants of the growing crop in which they are placed, and generate a detection signal that is representative of the sensed VOCs. The detection signal is communicated from the sensing devices 340, 344, 348, 352 to the controller 110 by a wired or wireless link. FIG. 4 shows one example schematic illustration of the component layout 460 of the sensing devices 340, 344, 348, 352.

The sensing devices include a Bluetooth Mesh (Bluetooth Low Energy) interface 462 to send and receive data, a GPS module 464 in order to periodically synchronize its real time clock as well as report GPS coordinates if needed, and a low power microcontroller 466 for performing analog-to-digital converter (ADC) sampling and scheduling events, as well as hardware 468 for interfacing with a sensor module 470, which includes a sensor 472.

In some embodiments, the sensors 336, 344, 352 may include an optical or other sensor configured to detect a diameter 'd of a stalk of the plant 306. For example, the sensors 336, 344, 352 may include one or more camera configured to generate an image. The sensor may recognize colors in the image to differentiate the plant 306 from a background and thereby calculate the diameter d. The sensors 336, 344, 352 may be located a known distance from the stalk, or may determine a distance to the stalk, such as by geolocation, radar, laser, lidar, etc. If the distance from the stalk is known, distances in an image can be calculated. In some embodiments, a detected image may be compared to a database of stored images to understand if a stalk diameter is smaller than expected and therefore potentially nutrient stressed. That determination along with detection of VOCs may be used to determine nutrient deficiency.

As another example, the diameter d may be detected by a non-contact caliper measurement, such as by using a laser beam as described in U.S. Pat. No. 9,581,433, "Caliper Sensor and Method Using Mid-infrared Interferometry," granted Feb. 28, 2017. In other embodiments, a jaw caliper carried by a vehicle may contact opposite sides of the stalk to determine the stalk diameter d.

Detection of the diameter d may be performed in addition to or instead of detection of VOCs. For maize plants, the stalk diameter d may be used to reliably detect nitrogen deficiency, either alone or in combination with VOC information.

The controller 110 is configured to process the detection signals from the sensing devices 102 (including the stalk diameter d, if detected) and generate a nutrient status indicator of the crop 106. In one embodiment, the nutrient status indicator is as simple as a qualitative indication as to whether a crop 106 is demonstrating regular growth or is stressed due to nutrient deficiency. In another embodiment, the nutrient status indicator provides an indication of the nutrient or nutrients for which the crop 106 is deficient, for example nitrogen or phosphorus. In yet another embodiment, the nutrient status indicator provides a quantitative indication of a nutrient deficiency or status of the crop 106.

A benefit of using information about VOCs and/or stalk diameter d is that nutrient deficiency can be reliably detected earlier than by conventional methods. For example, conventional visual inspection and tissue collection methods can reliably detect nutrient (e.g., nitrogen) deficiency when a maize plant has at least 12 leaves (which may be referred to in the art as growth stage V12). By using information about VOCs and/or stalk diameter d, nutrient deficiency can be reliably detected when a maize plant has only 6 leaves (which may be referred to in the art as growth stage V6). Earlier detection may enable an operator to correct the nutrient deficiency earlier, thus improving yield at the end of the season. Early deficiency detection may make a difference between profit and loss in the crop, by reducing the amount of nutrient required over the crop cycle of a plant, preserving yield potential, reducing input costs, and improving sustainability.

The nutrient status indicator is preferably displayed on a user interface device such as a display device. This provides valuable information to the grower to make crop-management decisions. For example, an indication of crop stress due to early-onset nitrogen deficiency may trigger the grower to make an application of nitrogen fertilizer to the crop 106.

Turning back to FIG. 1, the sensing devices 102 can be configured as a mesh network which can be deployed in a spaced relationship across the crop field 104. By employing a mesh network, each device 102 may communicate with one or more adjacent devices 102, which together cover many acres of land (that is, not all of the devices 102 need communicate directly with the controller 110). The controller 110 may be configured to receive a geolocation of each of the sensing devices 102 and generate a map that is representative of the crop field 104. The map is displayed to a user and presents a nutrient status indicator or metric that corresponds to the position of each sensing device 102.

Further to the displaying of the nutrient status indicator, the controller 110 may be configured to generate a crop application recommendation that is dependent upon the nutrient status indicator. The crop application recommendation may be displayed by a display device. The application recommendation may, for example, include a suggested fertilizer product, rate and timing, and be used by a grower in crop-management decisions. The application recommendation may also take account of the growth stage of the crop 106 (e.g., as determined by the number of leaves).

Although the system and method have application in a multitude of different crops and agronomic metrics, the system and method may be particularly suited for the monitoring of nitrogen status in maize crops.

Figure 5:
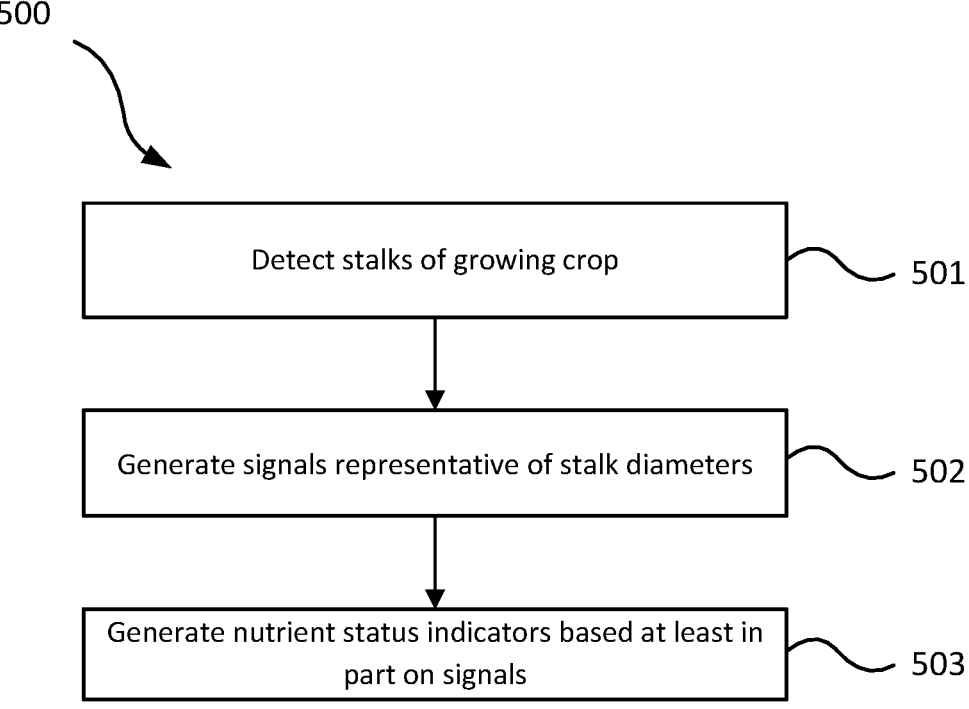
FIG. 5 is a process flow of a crop monitoring method in accordance with an embodiment.

In another embodiment, a method of monitoring crops is shown in FIG. 5, in which stalks of growing crop are detected 501, signals representative of stalk diameters are generated 502, and nutrient status indicators are generated 503, based at least in part on the signals representing the stalk diameters. In some embodiments, VOCs are also detected and used to generate the nutrient status indicators.

From reading the present disclosure, other modifications will be apparent to persons skilled in the art. Such modifications may involve other features which are already known in the field of crop monitoring systems and component parts thereof and which may be used instead of or in addition to features already described herein.

The invention claimed is:

1. A crop monitoring system comprising:
   a first sensor configured to sense a stalk of a growing crop and generate a detection signal representative of a diameter of the stalk;
   a second sensor configured to detect VOCs emitted by the growing crop and generate a VOC detection signature;
   a processor in communication with the first and second sensors, wherein the processor is configured to receive a geolocation of each sensor, generate a map representative of the crop field, and generate a nutrient status indicator from the detection signal and the VOC detection signature, the nutrient status indicator indicating whether the growing crop corresponding to the geolocation is stressed due to nutrient deficiency; and a user interface device in communication with the processor and configured to display the map comprising the nutrient status indicator corresponding to the first and second sensors.

2. The crop monitoring system of claim 1, wherein the first sensor comprises an optical sensor.

3. The crop monitoring system of claim 2, wherein the first sensor comprises a camera.

4. The crop monitoring system of claim 1, wherein the first sensor comprises a vehicle-mounted sensor configured to sense stalks of the growing crop as a vehicle carrying the first sensor is driven over a field containing the growing crop.

5. The crop monitoring system of claim 1, wherein the first sensor comprises at least one autonomous crop-scouting machine, wherein each crop-scouting machine comprises a sensor in wireless communication with the processor and adapted to sense stalks of the growing crop.

6. The crop monitoring system of claim 1, wherein the first sensor comprises a transmitter configured to send a signal to the processor.

7. The crop monitoring system of claim 1, wherein the first sensor comprises a communicatively connected mesh of sensors distributed across the crop field.

8. The crop monitoring system of claim 1, wherein the processor is configured to generate a crop application recommendation that is dependent upon the nutrient status indicator, wherein the user interface device is configured to display the crop application recommendation.

9. The crop monitoring system of claim 8, wherein the processor is configured to receive a crop growth stage indicator, and wherein the crop application recommendation is generated based upon the crop growth stage indicator.

10. The crop monitoring system of claim 8, wherein the crop application recommendation comprises a nitrogen application recommendation.

11. A method of monitoring a growing crop, the method comprising:

detecting a plurality of stalks of a growing crop and generating a plurality of signals representative of diameters of the stalks;

detecting at least one VOC emitted by the growing crop and generating a VOC detection signature; and generating a plurality of nutrient status indicators based at least in part on the signals and the VOC detection signature, the nutrient status indicators arranged as a map representative of a field in which the growing crop is located, the nutrient status indicator indicating whether the growing crop corresponding to a field location is stressed due to nutrient deficiency.

12. The method of claim 11, wherein detecting a plurality of stalks of a growing crop comprises generating a plurality of images representing the stalks.

13. The method of claim 11, wherein detecting a plurality of stalks of a growing crop comprises directing a laser beam toward the stalks.

14. The method of claim 11, wherein generating a plurality of nutrient status indicators comprises generating a plurality of nutrient status indicators of maize plants having fewer than 12 leaves.

15. The method of claim 11, further comprising generating and displaying a crop application recommendation that is dependent upon the nutrient status indicators.

16. The method of claim 15, wherein the crop application recommendation comprises a nitrogen application recommendation.

17. The method of claim 15, further comprising receiving a crop growth stage indicator, and wherein the crop application recommendation is generated based upon the crop growth stage indicator.

18. The method of claim 11, wherein detecting a plurality of stalks of a growing crop comprises navigating at least one autonomous crop-scouting machine through the field, wherein each crop-scouting machine comprises at least one sensor adapted to detect stalks of the growing crop.

\* \* \* \* \*